(12) United States Patent
Seo et al.

(10) Patent No.: US 7,915,434 B2
(45) Date of Patent: Mar. 29, 2011

(54) METHOD FOR PRODUCING PROPYLENE OXIDE

(75) Inventors: Tateo Seo, Chiba (JP); Hiroaki Abekawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/226,730

(22) PCT Filed: Apr. 26, 2007

(86) PCT No.: PCT/JP2007/059433
§ 371 (c)(1),
(2), (4) Date: Apr. 6, 2009

(87) PCT Pub. No.: WO2007/126138
PCT Pub. Date: Nov. 8, 2007

(65) Prior Publication Data
US 2009/0270641 A1    Oct. 29, 2009

(30) Foreign Application Priority Data

Apr. 27, 2006 (JP) ................................ 2006-123128

(51) Int. Cl.
*C07D 301/12* (2006.01)
(52) U.S. Cl. ...................................................... 549/531
(58) Field of Classification Search .................. 549/531, 549/532, 533
See application file for complete search history.

(56) References Cited

U.S. PATENT DOCUMENTS

| 2003/0109725 A1 | 6/2003 | Hofen et al. |
| 2006/0173200 A1 | 8/2006 | Ishino et al. |
| 2007/0043226 A1 | 2/2007 | Müller et al. |
| 2010/0003173 A1 | 1/2010 | Müller et al. |

FOREIGN PATENT DOCUMENTS

| CN | 1425011 A | 6/2003 |
| CN | 1756749 A | 4/2006 |
| JP | 2004-269380 A | 9/2004 |
| JP | EP 1489075 A1 * | 12/2004 |
| WO | WO 01/57009 | 8/2001 |
| WO | WO 02/092586 | 11/2002 |
| WO | WO 2004/078740 | 9/2004 |
| WO | WO2004/099166 A1 | 11/2004 |

OTHER PUBLICATIONS

Notification of Office Action issued Jul. 30, 2010, in corresponding Chinese Application 200780015168.8.
European Search Report, dated Nov. 12, 2010, in corresponding Application EP 07742868.8.

* cited by examiner

*Primary Examiner* — Janet L Andres
*Assistant Examiner* — David E Gallis
(74) *Attorney, Agent, or Firm* — Fitch, Even, Tabin & Flannery

(57) ABSTRACT

A method for producing propylene oxide comprising a step of reacting hydrogen peroxide with propylene in the presence of an epoxidation catalyst in a liquid phase to produce propylene oxide and a step of recovering a recyclable constituent in a vent gas generated in the above step by absorbing the recyclable constituent in a solvent containing a nitrile.

7 Claims, 2 Drawing Sheets

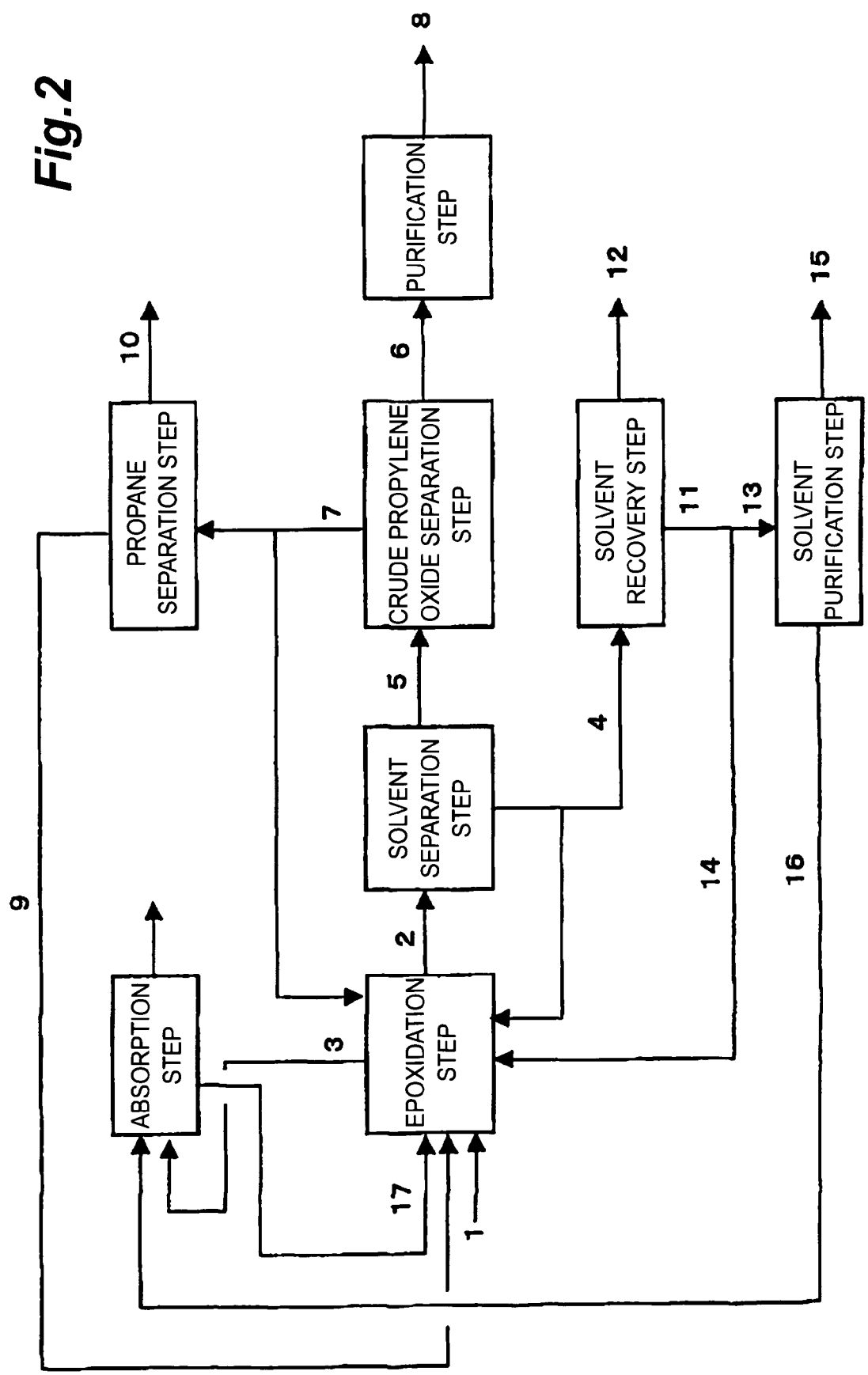

METHOD FOR PRODUCING PROPYLENE OXIDE

CROSS-REFERENCE TO RELATED APPLICATIONS

This is a U.S. National Phase of International Application PCT/JP2007/059433, filed Apr. 26, 2007, and claims the benefit of foreign priority under 35 U.S.C. §119 based on JP 2006-123128, filed Apr. 27, 2006, the entire disclosures of which applications are hereby incorporated herein by reference.

TECHNICAL FIELD

The present invention relates to a method for producing propylene oxide by performing epoxidation reaction of propylene, comprising a step of effectively recovering unreacted propylene and propylene oxide and the like in the vent gas.

BACKGROUND ART

In the method for producing propylene oxide by epoxidating propylene, as a method for recovering propylene and propylene oxide in the vent gas discharged from the separation step after the epoxidation reaction, it has been suggested to contact the gas discharged from the separation step with an alcohol such as methanol, a glycol, a cyclic ether, a glycol ether or a ketone to recover propylene and propylene oxide and to recycle propylene (see, for example, Patent document 1: WO 01/57009).

DISCLOSURE OF THE INVENTION

The above patent document describes that methanol is particularly preferably used as a reaction solvent but the methanol solvent has problems such that the absorption efficiency for unreacted propylene and the like is not necessarily sufficient. The present invention solves such problems in the epoxidation reaction and provides a method for producing propylene effectively.

That is, the present invention relates to a method for producing propylene oxide comprising a step of reacting hydrogen peroxide with propylene in the presence of an epoxidation catalyst in a liquid phase to produce propylene oxide and a step of recovering a recyclable constituent in a vent gas generated in the above step by absorbing the recyclable constituent in a solvent containing a nitrile.

BRIEF DESCRIPTION OF THE DRAWINGS

FIG. 2 is an example of a block flow diagram of a typical method for producing propylene oxide in the present invention, illustrating an example of a method in which hydrogen peroxide is synthesized from hydrogen and oxygen in the system, a mixed solvent of acetonitrile and water is used in the epoxidation step, and an acetonitrile solvent is obtained by removing water in the solvent purification step from the mixed solvent of acetonitrile and water obtained in the solvent recovery step and the acetonitrile solvent is used in the absorption step.

BEST MODE FOR CARRYING OUT THE INVENTION

Figure 1:
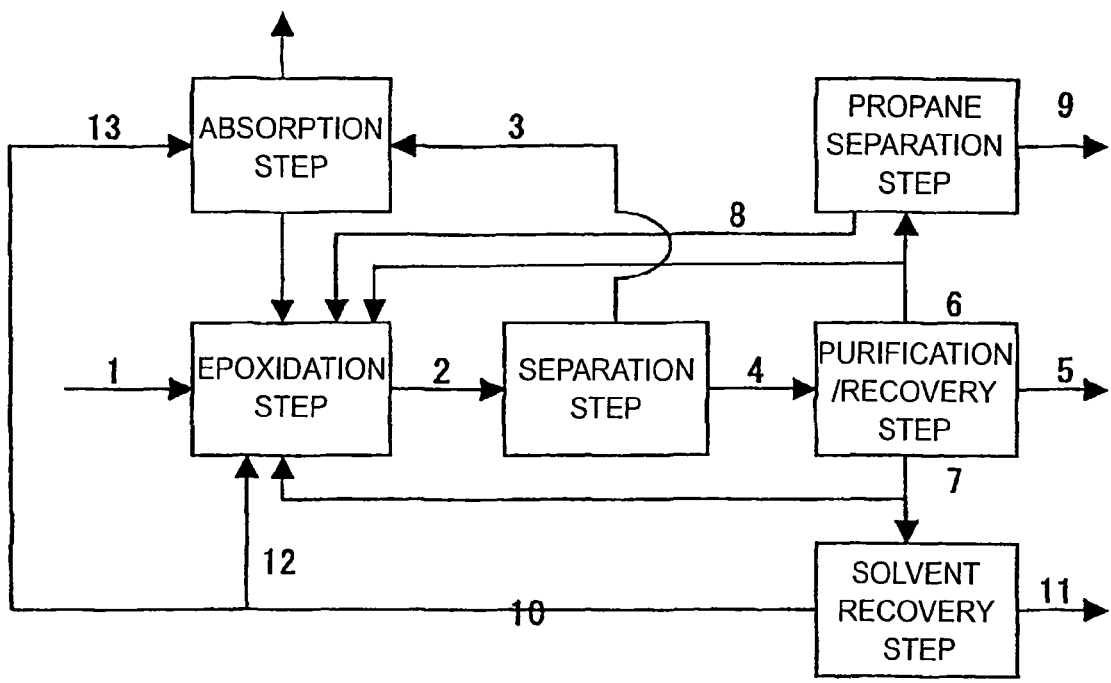
FIG. 1 is an example of a block flow diagram of a typical method for producing propylene oxide in the present invention, illustrating an example of a method in which hydrogen peroxide is supplied, a mixed solvent of acetonitrile and water is used in the epoxidation step, and the same mixed solvent of acetonitrile and water as the solvent used in the epoxidation step is used in the absorption step.

Hydrogen peroxide or hydrogen peroxide generated from hydrogen and oxygen in the reaction system is used for the epoxidation reaction of propylene.

The method for performing epoxidation reaction of propylene with hydrogen peroxide in the present invention is described.

As a catalyst for performing epoxidation reaction of propylene with hydrogen peroxide, titanosilicate catalysts can be included.

As a supplying method of hydrogen peroxide, a method of supplying a hydrogen peroxide solution produced beforehand or a method of synthesizing and supplying hydrogen peroxide in the reaction system can be included. As a method of synthesizing hydrogen peroxide in the reaction system, a method of using a transition metal catalyst such as Pd and Au which synthesizes hydrogen peroxide in the system by allowing the catalyst supported on or mixed with a catalyst for the epoxidation reaction thereby synthesizing hydrogen peroxide from hydrogen and oxygen can be included.

In the case of supplying a hydrogen peroxide solution produced beforehand, the concentration of hydrogen peroxide in the hydrogen peroxide solution is typically 0.1 to 70% by weight. As a hydrogen peroxide solution, a hydrogen peroxide aqueous solution or a mixed solution of hydrogen peroxide, water and an organic solvent can be included.

The epoxidation reaction of propylene according to the present invention can be performed at a reaction temperature of around 0° C. to 150° C. and at a reaction pressure of around 0.1 MPa to 20 MPa.

As a reaction method, a fixed bed flow reactor system or a slurry reactor system can be included. As a solvent of the epoxidation reaction, a single kind of nitrile, a mixed solvent of two or more kinds of nitrites, or a mixed solvent of a nitrile and water, alcohol, a mixed solvent of alcohol and water can be included. Examples of the nitrile include acetonitrile, propionitrile and benzonitrile. As alcohol, methanol, ethanol, 1-propanol, 2-propanol, n-butanol, sec-butanol, t-butanol as a single solvent or a mixed solvent of two or more kinds of these can be included. Acetonitrile, a mixed solvent of acetonitrile and water, methanol or a mixed solvent of methanol and water are industrially preferable in that they are easily available and inexpensive. In addition, acetonitrile and methanol are preferable in that they facilitate process construction since they are water-soluble and form a homogeneous liquid phase. Unreacted propylene, which is a recyclable constituent, is contained as a representative constituent in the vent gas generated in the separation step after the epoxidation step. Also, propylene oxide as a reaction product may be contained in the vent gas, which is a constituent which is recyclable for the epoxidation step. Inexpensive propylene oxide can be produced without requiring a large amount of energy, which is the case in distilling a recyclable constituent to separate, by recovering the recyclable constituent contained in the vent gas by absorbing the recyclable constituent in a solvent containing a nitrile.

In a method for producing propylene oxide by performing epoxidation reaction of propylene with a hydrogen peroxide, oxygen may be by-produced by decomposition of hydrogen peroxide in the reaction system and this may be accumulated to a high concentration level resulting in an explosive gas mixture with an organic compound, and in order to avoid dangers of the generated oxygen to produce an explosive gas mixture while supplying an inert gas to the reaction system, an inert gas such as nitrogen and carbon dioxide, methane, ethane or propane may be supplied to the reaction system in some cases. On this account such an inert gas and the like may be contained in the vent gas depending on cases.

In a method for synthesizing hydrogen peroxide from oxygen and hydrogen in the system and using the hydrogen peroxide in the epoxidation reaction, when, for example, an inexpensive oxygen source such as pressured air and oxygen containing a little amount of nitrogen generated by PSA (Pressure Swing Adsorption) is used, these inert gases are also contained in the vent gas.

When hydrogen peroxide is synthesized from oxygen and hydrogen in the system and used in the epoxidation reaction, there is a case in which propylene burns to by-produce carbon dioxide. In addition, when air, which is inexpensive, is used as an oxygen source, inert gases such as nitrogen and carbon dioxide, which are inert to the epoxidation of propylene, and impurities in propylene may accumulate in the vent gas in some cases and these impurities, inert gases and the like can be drawn out of the system as a vent gas.

As a solvent containing a nitrile used for recovering propylene oxide and unreacted propylene from the vent gas, a single kind of nitrile, a mixed solvent of two or more kinds of nitrites, or a mixed solvent of a nitrile and water can be included. Examples of the nitrile include acetonitrile, propionitrile and benzonitrile. It is preferable that the solvent is the same as used in the epoxidation reaction from a viewpoint of easiness in recovering the solvent. When a mixed solvent of water and a nitrile which forms a homogeneous phase with water is used as a reaction solvent, it is ordinarily preferable to perform the reaction in a composition with a more water content than the azeotropic composition from a viewpoint of reducing the energy for recovery procedure. However, use of a solvent miscible with water (forming a homogeneous phase) in the absorption step is disadvantageous since the melting point thereof is higher than that of the nitrile alone and therefore the lower limit temperature is restricted when cooled so as to reduce loss of recyclable constituents to the vapor phase part in the absorption step.

Therefore, when a mixed solvent of a nitrile and water which forms a homogeneous phase with water is used as a reaction solvent, it is more preferable that the solvent is recovered from the mixed solvent in the solvent recovery step at first and subsequently a part of the recovered solvent is supplied to the solvent purification step to separate water and then supplied to the absorption step as a solvent having a composition with less water content.

The water content of the solvent supplied to the absorption step is set depending on the number of stages of the distilling tower, reflux ratio and melting point at the time of cooling but it is typically not higher than 1% by weight, preferably not higher than 0.1% by weight.

The absorber liquid containing the nitrile which has absorbed propylene and propylene oxide obtained in the absorption step is supplied to the epoxidation step as it is when the solvent in the epoxidation step is the same as in the absorption step. When the solvent in the epoxidation step is different from that in the absorption step, the recyclable constituents are distilled and separated and after that, the recyclable constituents alone are supplied to the epoxidation step or water is additionally supplied to the absorber liquid so as to adjust the solvent composition to the solvent composition in the epoxidation step and then the mixture is supplied to the epoxidation step. In the case that water is additionally supplied, deficient water may be additionally supplied so as to adjust the water content in accordance with the composition of the reaction solvent in the epoxidation step when the absorber liquid is supplied to the epoxidation step.

Examples of the method adopted in the solvent purification step for separating water from a mixed solvent of a nitrile and water which forms a homogeneous phase with water as a reaction solvent include a method of using an adsorbent such as molecular sieve and zeolite and a method of removing water from the nitrile by distillation. In the case of a nitrile such as acetonitrile which forms an azeotrope with water and has correlation between the pressure of the system and the azeotropic composition, a separation method can be included in which rectification is performed at a pressure to give an azeotropic composition with a high nitrile concentration at first so that water and acetonitrile are distilled out from the top of the tower and then rectification is performed at a pressure to give an azeotropic composition with a low nitrile concentration so that the nitrile with a low water concentration is obtained from the bottom of the tower.

As an epoxidation catalyst preferably used in the case of using a solvent containing a nitrile as a reaction solvent, titanosilicates such as crystalline titanosilicate having an MWW structure and a layered precursor of crystalline titanosilicate having an MWW structure are exemplified. As a titanosilicate catalyst, a titanosilicate catalyst having a pore structure of a 12-membered oxygen ring or more is preferable in the point that high activity can be attained at the time of using a solvent containing a nitrile and a Ti-MWW catalyst and a layered titanosilicate catalyst are more preferable. The Ti-MWW is a crystalline titanosilicate having a MWW structure, a Framework Type Code defined by IZA (International Zeolite Association). For example, layered precursors of Ti-MWW zeolite described in Chemistry Letters, 774-775, (2000) are known as layered titanosilicates. For example, it can be confirmed from X-ray diffraction peaks that a Ti-MWW zeolite precursor has a layered structure as described in Shokubai (Catalyst and Catalysis), 158, Vol. 43, (2001).

The present invention is described by way of FIG. 1 and FIG. 2 which are examples of block flow diagrams illustrating the process flow for producing propylene oxide in the present invention.

In FIG. 1, fluid 1 is propylene, hydrogen peroxide water, acetonitrile and an inert gas. Fluid 2 is epoxidation reaction distillate. The fluid 2 is separated into gas fluid 3 and liquid fluid 4 in the separation step. The liquid fluid 4 is separated into fluid 5, fluid 6, and fluid 7 in the separation/purification step, and they are subjected to production, recycling and purging. Product propylene oxide can be taken out as fluid 5. Fluid 6 mainly consists of propylene and propane. A part of the fluid 6 is recycled to the epoxidation step, and another part thereof is sent to the propane separation step. Typically in the propane separation step, propylene is recovered from the top of the tower (fluid 8) and propane is separated from the bottom of the tower (fluid 9). The recovered propylene (fluid 8) is supplied again to the epoxidation step. Fluid 7 mainly consists of water and acetonitrile, and sometimes contains propylene glycol, oligomers thereof or the like. A part of the fluid 7 is recycled to the epoxidation step, and another part thereof is sent to the solvent recovery step. In the solvent recovery step, acetonitrile and water in an azeotropic composition are recovered from the top of the tower (fluid 10) and water and high boiling point compounds such as propylene glycol and oligomers are separated from the bottom of the tower, and a part thereof is sent to the disposal step (fluid 11) and the remainder is supplied to the epoxidation step (fluid 12) and the absorption step (fluid 13) which recovers recyclable constituents in the vent gas. The gas fluid 3 separated at the separation step contains an inert gas, propylene, oxygen and propylene oxide. A part of the fluid 3 is purged from the vent line, and the remainder is supplied to the absorption step. In the absorption step, the fluid 3 is contacted with a mixture (fluid 13) of acetonitrile and water obtained in the solvent recovery step, thereby propylene and propylene oxide are recovered, and the fluid is supplied again to the epoxidation step. The remaining gas fluid after recyclable constituents are recovered therefrom is purged to the outside of the system.

In FIG. 2, fluid 1 is propylene, hydrogen, oxygen, nitrogen, acetonitrile, water and an inert gas. Fluid 2 is an epoxidation reaction solution, and fluid 3 is an epoxidation reaction gas. The fluid 2 is supplied to the solvent separation step, and the fluid 3 is supplied to the absorption step. The fluid 2 mainly consists of acetonitrile, water, propylene oxide, propylene, propylene glycol and propane whereas the fluid 3 mainly consists of hydrogen, oxygen, nitrogen, propylene oxide, propylene and propane. In the solvent separation step, the fluid 2 is separated into fluid 4 mainly composed of acetonitrile, water and propylene glycol which are high boiling point constituents and fluid 5 mainly composed of propylene oxide, propylene and propane which are low boiling point constituents. The fluid 5 is separated in the crude propylene oxide separation step into fluid 6 mainly composed of propylene oxide and fluid 7 mainly composed of propylene and propane. In the purification step, the fluid 6 is purified to the product (fluid 8) as a purified propylene oxide. A part of the fluid 7 is recycled to the epoxidation step and another part thereof is sent to the propane separation step. In the propane separation step, propylene is typically recovered from the top of the tower (fluid 9) and propane is separated from the bottom of the tower (fluid 10). The recovered propylene (fluid 9) is supplied again to the epoxidation step. A part of the fluid 4 mainly composed of acetonitrile, water and propylene glycol is recycled to the epoxidation step, and another part thereof is sent to the solvent recovery step. In the solvent recovery step, acetonitrile and water in an azeotropic composition are recovered from the top of the tower (fluid 11) and water and high boiling point compounds such as propylene glycol and oligomers are separated from the bottom of the tower and sent to the disposal step (fluid 12). A part of the fluid 11 is sent to the solvent purification step (fluid 13) and the remainder is supplied to the epoxidation step (fluid 14). In the solvent purification step, a mixture of acetonitrile and water which is supplied in an azeotropic composition is separated into water having an acetonitrile content not higher than 1% (fluid 15) and acetonitrile having a water content not higher than 1% by weight (fluid 16) by pressure swing method. The fluid 15 is sent to the disposal step and the fluid 16 is supplied to the absorption step. In the absorption step, propylene oxide and propylene which are recyclable constituents are absorbed and recovered (fluid 17) by fluid 16 from fluid 3 mainly composed of hydrogen, oxygen, nitrogen, propylene oxide, propylene and propane. The fluid 17 is mainly composed of acetonitrile, propylene oxide and propylene. The fluid 17 is supplied again to the epoxidation reaction step. The remaining gas fluid after propylene oxide and propylene are recovered therefrom is purged to the outside of the system.

According to the present invention, propylene oxide and propylene in the vent gas can be recovered more effectively by absorbing propylene oxide and propylene in the vent gas using a nitrile solvent. As a preferable nitrile solvent, acetonitrile and propionitrile can be included.

The conditions for absorbing propylene oxide and propylene in the vent gas using a nitrile solvent typically include temperature of 0° C. to 80° C. (temperature of the absorber in the absorbing tower) and pressure of 0 MPa to 2 MPa (absolute pressure) of the absorbing tower. When the temperature is too high, absorption efficiency decreases, and when the temperature is too low, energy cost for cooling becomes excessive. When the pressure is too high, energy cost for compression becomes excessive, and when the pressure is too low, absorption efficiency decreases. As for a method for absorbing the recyclable constituents in the vent gas using a nitrile solvent, a method of dispersing the vent gas in the nitrile solvent with a sparger so as to increase the contact efficiency of the gas and the liquid thereby performing absorption, and a method of supplying a nitrile solvent from the upper part of an absorbing tower filled with packing so as to increase the contact area and supplying the gas from the lower part thereof thereby subjecting them to countercurrent contact and performing absorption are preferable methods.

EXAMPLES

The present invention will now be explained with reference to examples, but the present invention is not limited to these working examples.

Example 1

The present invention is described by way of an example. That is, gases in which propylene gas was controlled to $3.3 \times 10^{-7}$ $m^3/s$ and nitrogen gas to $3.0 \times 10^{-6}$ $m^3/s$ were mixed at 26° C. under atmospheric pressure using a thermal mass flow controller and were bubbled into 0.10 kg of an acetonitrile solvent. Sampling was performed by taking out the solution 30 minutes later after starting absorption. Analysis was performed using gas chromatography. The result revealed that propylene absorption amount per unit weight of the solvent was 0.0477 mol/kg.

Comparative Example 1

An experiment was performed in the same way as in Example 1 except that a methanol solvent was used in place of the acetonitrile solvent. The result revealed that propylene absorption amount per unit weight of the solvent was 0.0425 mol/kg.

TABLE 1

| | Feeding rate of propylene gas ($\times 10^{-7}$ $m^3/S$) | Feeding rate of nitrogen gas ($\times 10^{-7}$ $m^3/S$) | Volume ratio of propylene gas/nitrogen gas | Propylene absorption amount mol/kg-solvent |
|---|---|---|---|---|
| Example 1 | 3.3 | 30 | 10/90 | 0.0477 |
| Comparative Example 1 | 3.3 | 30 | 10/90 | 0.0425 |

Example 2

Example of the Experiment Shown in Block Flow Diagram of FIG. 2

Epoxidation Step

After 131 g of acetonitrile water having an acetonitrile/water weight ratio of 80/20, 2.276 g of Ti-MWW catalyst and 1.056 g of a catalyst containing 1% palladium on activated carbon were placed in a 300 cc autoclave, the pressure was adjusted to 4 MPa in absolute pressure with nitrogen and the temperature in the autoclave was adjusted to 60° C. by circulating warm water in the jacket. To the autoclave, a mixed gas having a composition of 3.8% by volume of hydrogen, 8.9% by volume of oxygen and 87.3% by volume of nitrogen at 143 NL/Hr, an acetonitrile water (in which the weight ratio of acetonitrile/water was 80/20) which contains 0.7 mmol/kg of anthraquinone and 0.7 mmol/kg of ammonium dihydrogenphosphate at 90 g/Hr, and a propylene liquid containing 0.4% by volume of propane at 31.0 g/h were supplied continuously. During the reaction, the reaction temperature was controlled to 60° C. and the reaction pressure to 4 MPa. The Ti-MWW catalyst and palladium catalyst on activated carbon, which were solid constituents, were filtered with a sintered filter and 91.9 g/Hr of a fluid component and 200.9 g/Hr of a gas component were taken out continuously. At the same time, the reaction solution gas was sampled and it was returned to atmospheric pressure to be separated into a fluid component and a gas component and each of them were subjected to composition analysis by gas chromatography. The result revealed that 4.09 g/Hr of propylene oxide, 0.68 g/h of propylene glycol and 0.55 g/Hr of propane were generated whereas 27.1 g/Hr of propylene, 1.31 NL/Hr of hydrogen and 9.92 NL/Hr of oxygen remained unreacted. Conversion ratio of propylene was 12.5% (for propylene supplied to the reactor) and selectivity based on the converted propylene was 76.6%. In the meantime, selectivity based on the converted hydrogen was 36.7%.

Separation/Recovery/Absorption Step

In the absorption step, an acetonitrile solvent obtained by separating water in the solvent purification step from the mixed solvent of acetonitrile and water obtained in the solvent recovery step was used.

With regard to these steps, the results of calculation simulation which was performed based on known physical properties data and the absorption data of Example 1 are shown below.

When a gas-liquid separation simulation of a fluid component and a gas component taken out of the reactor at 60° C., 4 MPa is performed, a gas of 24.1 g/Hr of propylene, 0.6 g/Hr of propane, 1.3 g/Hr of propylene oxide, 4 g/Hr of acetonitrile, 0.7 g/Hr of water, 0.1 g/Hr of hydrogen, 14.2 g/Hr of oxygen and 156 g/Hr of nitrogen is obtained. When a simulation in which this gas is fed from the bottom of the tower with 20 theoretical stages and acetonitrile of 25° C. is fed at a rate of 1000 g/Hr from the top of the tower to subject them to countercurrent contact is performed, the exhausted gas from the top of the tower contains very little of propylene and propylene oxide which are recyclable constituents and a recovery liquid of 24.1 g/Hr of propylene, 0.6 g/Hr of propane, 1.3 g/Hr of propylene oxide, 1002.748 g/h of acetonitrile, 0.7 g/Hr of water and 0.074 g/Hr of oxygen was obtained from the bottom of the tower.

INDUSTRIAL APPLICABILITY

According to the method of the present invention, propylene oxide can be advantageously produced.

The invention claimed is:

1. A method for producing propylene oxide, comprising
   a step of reacting hydrogen peroxide with propylene in the presence of an epoxidation catalyst in a liquid phase to produce propylene oxide,
   a step of separating water from a solvent containing a nitrile, wherein the solvent containing a nitrile is a solvent recovered from a reaction solution in the step of reacting hydrogen peroxide with propylene, and
   a step of recovering a recyclable constituent in a vent gas by absorbing the recyclable constituent in the solvent obtained by separating water, wherein said vent gas was generated in the step of reacting hydrogen peroxide with propylene.

2. The production method according to claim 1, wherein the recyclable constituent is propylene oxide or unreacted propylene.

3. The method for producing propylene oxide according to claim 1, which further comprises a step of subjecting a solution comprising a solvent having absorbed therein the recyclable constituent to epoxidation reaction.

4. The method according to claim 1, wherein the epoxidation catalyst is a titanosilicate catalyst having a pore of 12-membered oxygen ring or more.

5. The method according to claim 4, wherein the titanosilicate catalyst having a pore of 12-membered oxygen ring or more is a crystalline titanosilicate having an MWW structure or a precursor thereof.

6. The production method according to claim 2, wherein a solution comprising a solvent containing a nitrile having absorbed therein a recyclable constituent contained in the vent gas is subjected to epoxidation reaction.

7. A method for producing propylene oxide comprising:
   (a) reacting hydrogen peroxide with propylene in the presence of an epoxidation catalyst in a liquid phase to produce propylene oxide,
   (b) recovering a solvent containing a nitrile from a reaction solution after (a),
   (c) separating water from the solvent containing a nitrile, and
   (d) recovering a recyclable constituent in a vent gas by absorbing the recyclable constituent in the solvent recovered by (c), said vent gas being generated in (a), and
   (e) subjecting a solution comprising the solvent obtained by (d) to epoxidation reaction.

* * * * *